(12) United States Patent
Hummel et al.

(10) Patent No.: US 7,740,639 B2
(45) Date of Patent: Jun. 22, 2010

(54) METHOD AND DEVICE FOR THE ENDOSCOPIC APPLICATION OF SELF-CLOSING MEDICAL CLIPS

(75) Inventors: Christian Hummel, Süssen (DE); Gerhard Emberger, Süssen (DE); Rudolf Bauer, Hallerndorf (DE)

(73) Assignees: Carl Stahl GmbH, Süssen (DE); Medwork Medical Products and Services GmbH, Höchstadt/Aisch (DE)

( * ) Notice: Subject to any disclaimer, the term of this patent is extended or adjusted under 35 U.S.C. 154(b) by 528 days.

(21) Appl. No.: 10/565,735

(22) PCT Filed: Jul. 13, 2004

(86) PCT No.: PCT/EP2004/007694

§ 371 (c)(1),
(2), (4) Date: Jun. 14, 2006

(87) PCT Pub. No.: WO2005/009254

PCT Pub. Date: Feb. 3, 2005

(65) Prior Publication Data
US 2006/0271072 A1 Nov. 30, 2006

(30) Foreign Application Priority Data
Jul. 26, 2003 (DE) .............................. 103 34 083

(51) Int. Cl.
*A61B 17/10* (2006.01)
(52) U.S. Cl. .................. 606/142; 606/139; 606/143; 606/151; 606/157; 606/221
(58) Field of Classification Search .............. 606/142, 606/143, 139, 151, 157, 221
See application file for complete search history.

(56) References Cited

U.S. PATENT DOCUMENTS

| 4,416,266 A | 11/1983 | Baucom |
| 4,671,282 A | 6/1987 | Tretbar |
| 5,174,276 A | 12/1992 | Crockard |
| 6,814,742 B2 * | 11/2004 | Kimura et al. ............... 606/151 |

(Continued)

FOREIGN PATENT DOCUMENTS

| DE | 102 03 956 A1 | 9/2002 |
| DE | 101 50 829 A1 | 10/2002 |
| DE | 102 11 049 A1 | 10/2002 |
| DE | 102 22 857 A1 | 12/2002 |

*Primary Examiner*—(Jackie) Tan-Uyen T Ho
*Assistant Examiner*—Jing Ou
(74) *Attorney, Agent, or Firm*—Roylance, Abrams, Berdo & Goodman, L.L.P.

(57) ABSTRACT

A method and apparatus for the endoscopic application of self-closing medical clips (3), in particular, for arresting internal bleeding. The distal end of a catheter tube (1) is introduced into the body of a living being to be treated. Several clips (3), arranged successively in the catheter tube (1), are pushed forward in the direction of the tube distal end by a user device located at the proximal end of the catheter tube (1). The foremost clip (3) to be applied is pushed out of the distal end and opened by an actuation device. The actuation device includes an actuation element (21) which can be actuated by the user device, moved longitudinally into the catheter tube (1), and acts on the first front clip (3), as well as a control part (25) which converts the actuation force of the actuation element into an opening movement of the legs (5) of the clip (3). After the opening of the clip (3), the actuation element (21) is separated from the clip (3), for releasing the clip to close its legs (5) for application, and to functionally link with the following clip (3) in the catheter tube (1).

18 Claims, 6 Drawing Sheets

U.S. PATENT DOCUMENTS

| | | |
|---|---|---|
| 6,923,818 B2 * | 8/2005 | Muramatsu et al. .......... 606/142 |
| 7,011,667 B2 * | 3/2006 | Kobayashi et al. .......... 606/142 |
| 2002/0045909 A1 * | 4/2002 | Kimura et al. .............. 606/151 |
| 2002/0128667 A1 * | 9/2002 | Kobayashi et al. .......... 606/139 |
| 2002/0138083 A1 | 9/2002 | Muramatsu |
| 2002/0177861 A1 * | 11/2002 | Sugiyama et al. ........... 606/151 |

* cited by examiner

METHOD AND DEVICE FOR THE ENDOSCOPIC APPLICATION OF SELF-CLOSING MEDICAL CLIPS

FIELD OF THE INVENTION

The present invention relates to a method and device for endoscopic application of self-closing medical clips, especially for stopping internal hemorrhages, in which a catheter tube with its distal end is placed in the body of the living being to be treated.

BACKGROUND OF THE INVENTION

Different processes using flexible endoscopes are known for stopping internal hemorrhages, for example, in the upper or lower gastrointestinal tract from varicose hemorrhages, post-polypectomy hemorrhages or ulcerative hemorrhages. Examples include coagulation, sclerosing, ligature, or application of self-closing clips. All the known processes are subject to disadvantages in various respects, whether the therapeutic success is not satisfactory or use is complex or very expensive. Recently, as the preferred process, the clip procedure has become established as being relatively favorable, that is, subject to few disadvantages. Further applications of these clips can be found in the area of attaching markers for identification of diagnostic or x-ray sections and surgical treatment procedures, for example, removal of polyps in the gastrointestinal tract.

In the clip procedure, a metallic clip is pushed out of the distal end of a catheter tube, opened and placed at the hemorrhage site such that it forms a clamp which clamps off the hemorrhage. U.S. Pat. No. 5,174,276 shows a device designed for implementing this clip procedure.

When the clip procedure is being carried out, in many cases several clips are needed to stop the bleeding. In the known clip procedure, this disadvantageously leads to delays in the course of the treatment because the applicator device must be removed from the body each time for re-seating of clips, provided with another clip, reinserted into the body with the catheter tube and placed at the treatment site. This procedure leads not only to a prolongation of the course of treatment, which can result in serious danger to the patient in a case of heavy bleeding, but also entails the danger of faulty placement.

SUMMARY OF THE INVENTION

An object of the present invention is to provide a process which permits multiple placement of hemostatic clips in immediate succession, without the need to provide the endoscopic device with another clip outside of the body for each application.

This object is basically achieved by a process according to the present invention, where the catheter tube itself is used as a magazine which is loaded with several clips before implementing the pertinent treatment. Multiple application of hemostatic clips in immediate succession is made possible without the endoscopic device needing to be removed from the body after each clip application. Rather, the frontmost clip can be pushed out of the distal end of the catheter tube, opened by an actuating element acting on it, and placed on the hemorrhage site to be treated. The actuating element is detached from the clip so that it is released and its self-closing legs effect the hemostatic clamping, after which the actuating element is functionally linked to the clip which follows in sequence in the catheter tube, so that if necessary the next clip can be applied without delay. Preferably the clips are already loaded by the manufacturer. In particular, in the case of special applications it is also possible to magazine the clips on site, that is to say, at the site of the procedure. Preferably, flexible spiral tubes resistant to tension and compression, but also tube-like flexible application bodies can be used as the catheter tube.

Another object of the present invention is to provide a device for implementing the process. In the device of the present invention, a control part converts the actuation force of the actuating element, which can be controlled by the operator of the device into the opening motion of the legs of the clip. The control part is located on the distal end of a sleeve-like receiving part associated with the respective clip. The clip is shaped on its legs adjacent to each other such that when the clip is inserted into the receiving part, an opening motion of the free leg ends takes place by the kink of the two legs which forms an arch striking the control part. If, after opening the clip, the kink on the legs is disengaged from the sleeve-like receiving part by the actuating element, the legs of the clip are released again in order to be closed by their own elasticity at the application site. This closing process can be further promoted by deformation at the kink of the clip effected by the sleeve-like receiving part and, in certain configurations, can also be replaced exclusively by the indicated deformation.

The actuating element can be a pulling element, and the control part can be a beveled control surface located on the end edge of the sleeve-like receiving part. The opening and subsequent closing of the legs of the clip which is to be applied are effected by pulling the clip into its receiving part. The opening motion takes place by the kink of the legs striking the control surface. Subsequently pulling the kinks through the receiving part effects the clip legs being released for the closing motion as soon as the kinks of the legs have run through the sleeve-shaped receiving part. The beveled control surface can also be formed by the curved control surface's running convexly or concavely.

The pulling element can be a pull cable. To connect the pull cable to the clip, on the clip back end crosspiece connecting the legs, each clip can have two adjacent through holes. The cable extends through those holes in a loop, such that it extends in an advancing strand to the clip and back from the latter back in a retreating strand to the operator means. The section of the end crosspiece of the clip located between the through holes is made as a predetermined breaking point which can be broken by the pulling force of the pull cable acting by the loop. The pull cable can then be easily detached from the clip after completion of the actuating process.

The procedures of pulling the clip into the receiving part and of detaching the pull cable from the applied clip are especially safe, i.e., without the danger of the clip's changing location by the force applied by the pull cable at the predetermined breaking point. On the distal end of the catheter tube, a blocking element permits the passage of the sleeve-like receiving part with the respective clip only in the exit direction forward, and supports the sleeve-like receiving part against the motion effected by the pulling force of the pull cable.

In an especially advantageous manner, these embodiments can be further configured such that in the catheter tube there are several clips with the respective sleeve-like receiving part in succession. The pull cable with the advancing strand and with the retreating strand is guided in each case through one or the other through hole of the end crosspieces of all clips.

With such a structure of the device, several clips can be applied in direct succession. After the pull cable is pulled off, the applied clip the device is immediately functionally linked to the respective following clip by pulling on the pull cable. This action takes place by the pull cable on the end crosspiece of the following clip automatically forming a loop assembly. Thus, without any other measures being necessary, the device is immediately prepared for application of the following clip.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE INVENTION

Figure 1:
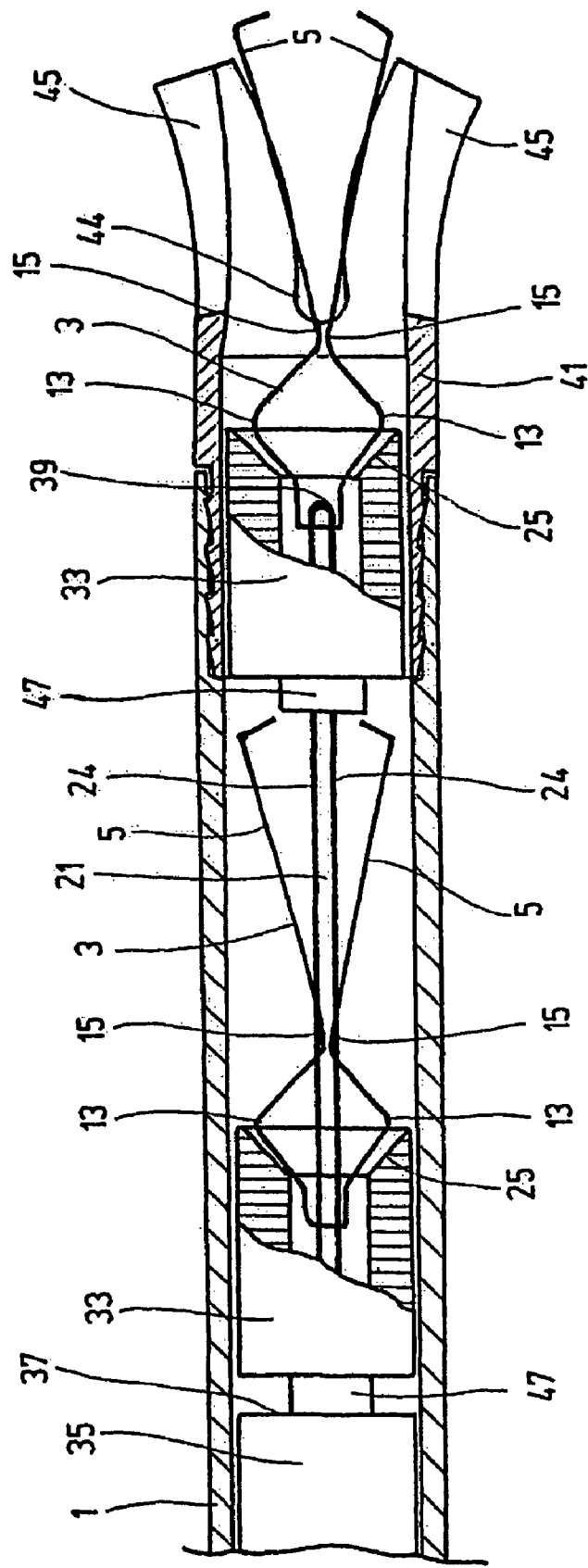
FIG. 1 is a schematically simplified, side elevational view in section of only the distal end section of the catheter tube as a component of the device according to one embodiment of the present invention, with this section being shown on an enlarged scale compared to the natural size.

FIG. 1 shows the distal end section of the catheter tube 1 as a component of an exemplary embodiment of the device of the present invention. The catheter tube 1 extends through the associated working space of a flexible endoscope which can be of conventional design in medical technology and which contains at least one other inner working space for endoscope optics including illumination and/or for other purposes (for example, suction). The proximal end (not shown) of the catheter tube 1 is functionally connected to the manipulation and operator means located on that end of the endoscope. The outside diameter of the catheter tube 1 is 2.7 mm corresponding to the clearance of the working spaces in flexible endoscopes.

Figure 2:
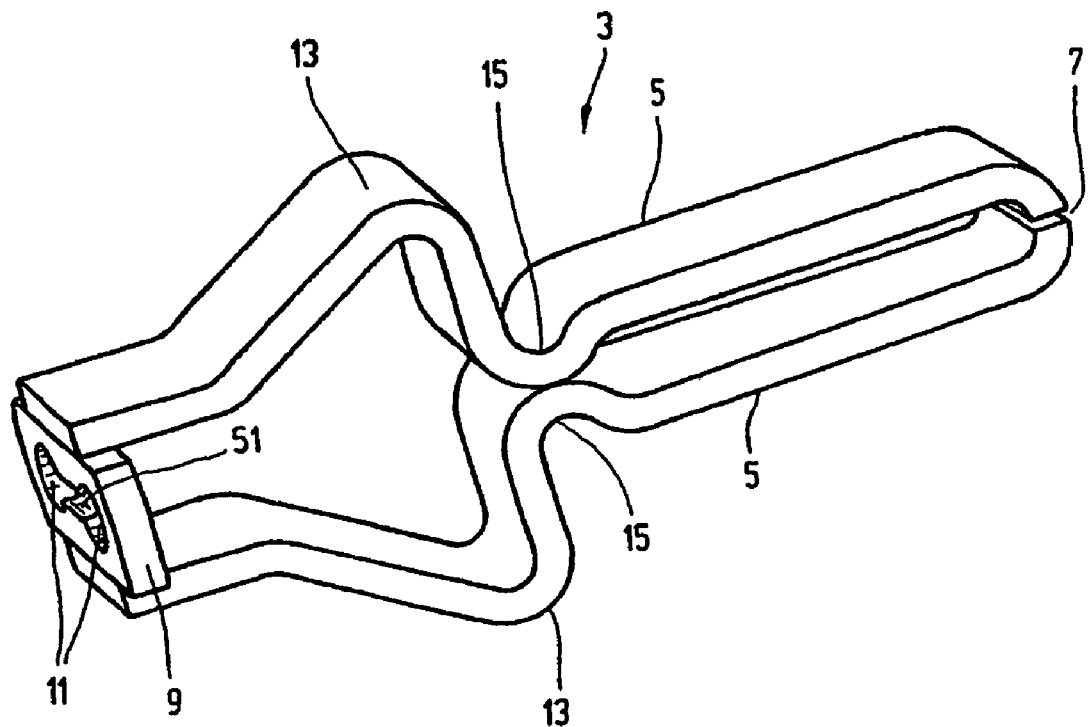
FIG. 2 is a perspective view of a self-closing medical clip drawn on a still larger scale, for use in the device of the present invention.
Figure 3:
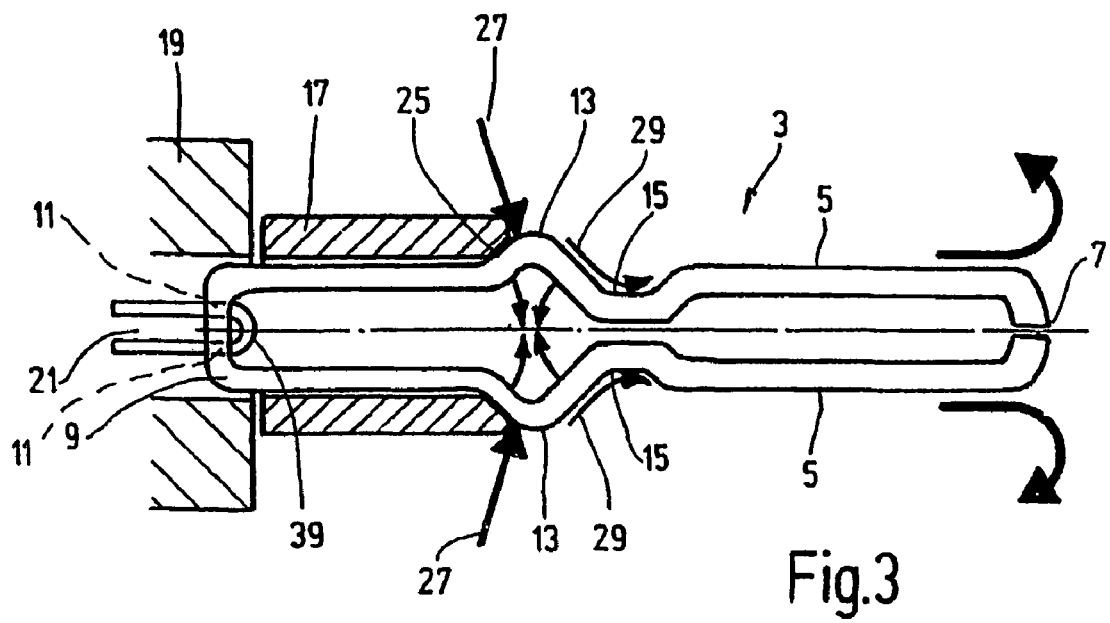
FIGS. 3 and 4 are schematic, side elevational views of the device of FIG. 1 illustrating the movements and forces for opening of the clip.
Figure 4:
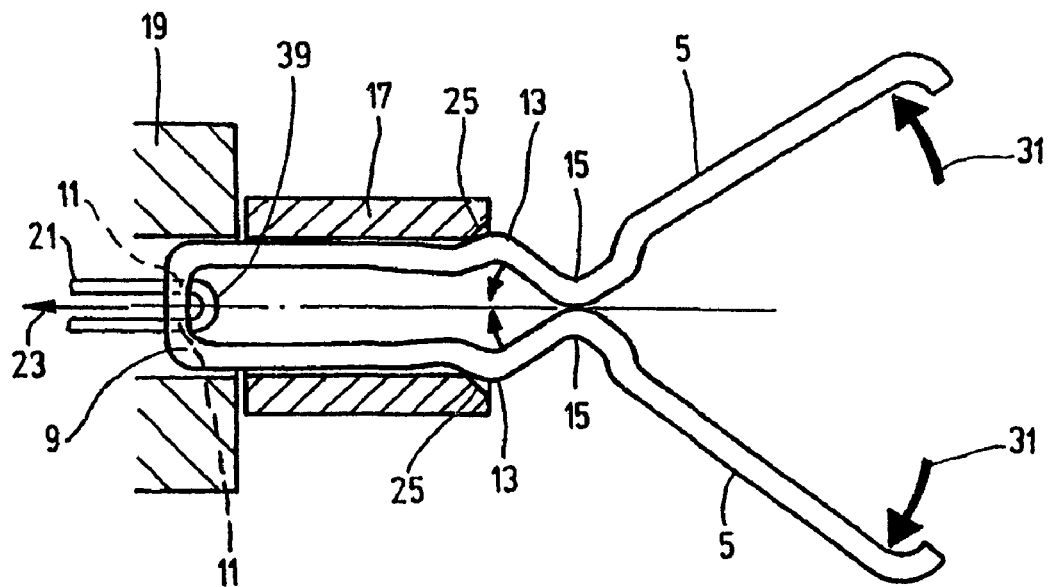

The device of the present invention is suited for application of self-closing medical clips 3 of a design as can be seen most clearly from FIGS. 2 to 4. The clip 3 is formed from a material such as high quality steel customarily used for medical purposes, and has two legs 5 which, without crossing one another, are adjacent to each other and are bent toward each other on the clip free leg end 7. On the end opposite the leg end 7, the legs 5 are connected to each other by an end crosspiece 9 having through two through holes 11 adjacent to each other. Offset from and between the end crosspiece 9 and the free leg end 7, each leg 5 has a first kink 13 arched to the outside and closer to end crosspiece 9 than to the leg end 7, and a second kink 15 arched to the inside and closer to the leg end 7 than the first kink. The second kinks is together form a support point for the mutual contact of the legs 5. From the second kink 15, the remaining sections of the legs 5 extend more or less parallel to each other to the free leg end 7 when the clip 3 is in the closed state, as is shown in FIGS. 2 and 3, i.e., the initial state of the clip 3.

The functional diagrams of FIGS. 3 and 4 using the sleeve 17 and a counter bearing 19 show the forces which effect opening of the legs 5 under the action of a pulling force applied by a pull cable 21 to the clip 3 corresponding to the action arrow 23 in FIG. 4. Upon contact with the beveled control surface 25 on the end edge of the sleeve 17, a force directed inwardly (see arrow 27) acts on each first kink 13, the legs 5 being extended (see arrows 29 in FIG. 3) with the second kinks 15 for mutual support. Due to the pulling force which continues to act (arrow 23), the legs 5 at the support point of the second kinks 15 seesaw on each other, which results in the opening-pivoting of the legs 5 according to arrows 31 (FIG. 4).

FIG. 1 shows the catheter tube 1 with several clips 3 in succession, each forming a unit with a sleeve-like receiving part 33. In its operation, the receiving part 33 corresponds in the interaction of its front control surface 25 with the respective clip 3 of the sleeve 17, as shown in FIGS. 3 and 4 to illustrate the forces acting on the clip 3. In FIG. 1, two clips 3 with the respective receiving parts 33 are accommodated in the catheter tube 1. But in practical application, the catheter tube 1 can be provided as a magazine for 2 to 10 clips, preferably for 2 to 5 clips or more. As FIG. 1 shows, the units including the clip 3 and receiving part 33 can be moved in the catheter tube 1 by a sliding tube 35 with a front end edge 37 forming a plunger for contact with the adjacent receiving part 33 and with a proximal end which can be manipulated as part of the actuating means from the operator means on the outer actuating end of the endoscope.

As is likewise apparent from FIG. 1 in conjunction with FIGS. 2 to 4, the pull cable 21 extends in the catheter tube 1 as the actuating element in two strands 24 through the through holes 11 (see FIG. 2) of each clip 3. On the frontmost clip 3, a loop 39 is formed on the end crosspiece 9 (FIG. 1). The loop 39 is also shown in the schematics of FIGS. 3 and 4. The strands 24 of the pull cable 21 are routed in the catheter tube 1 through the sliding tube 35 as the actuating element as far as the operator means on the outer end of the endoscope.

When the device is being used, the clips 3 are arranged in succession in the catheter tube 1 with the associated receiving parts 33, and are advanced by the sliding tube 35 until the receiving part 33 of the frontmost clip 3 has left the catheter tube 1, more precisely, has passed through a blocking element 41 mounted on the distal end of the catheter tube 1. After passing through the blocking element 41, this receiving part 33 with the respective clip 3 is in the position shown in FIG. 5.

Figure 14:
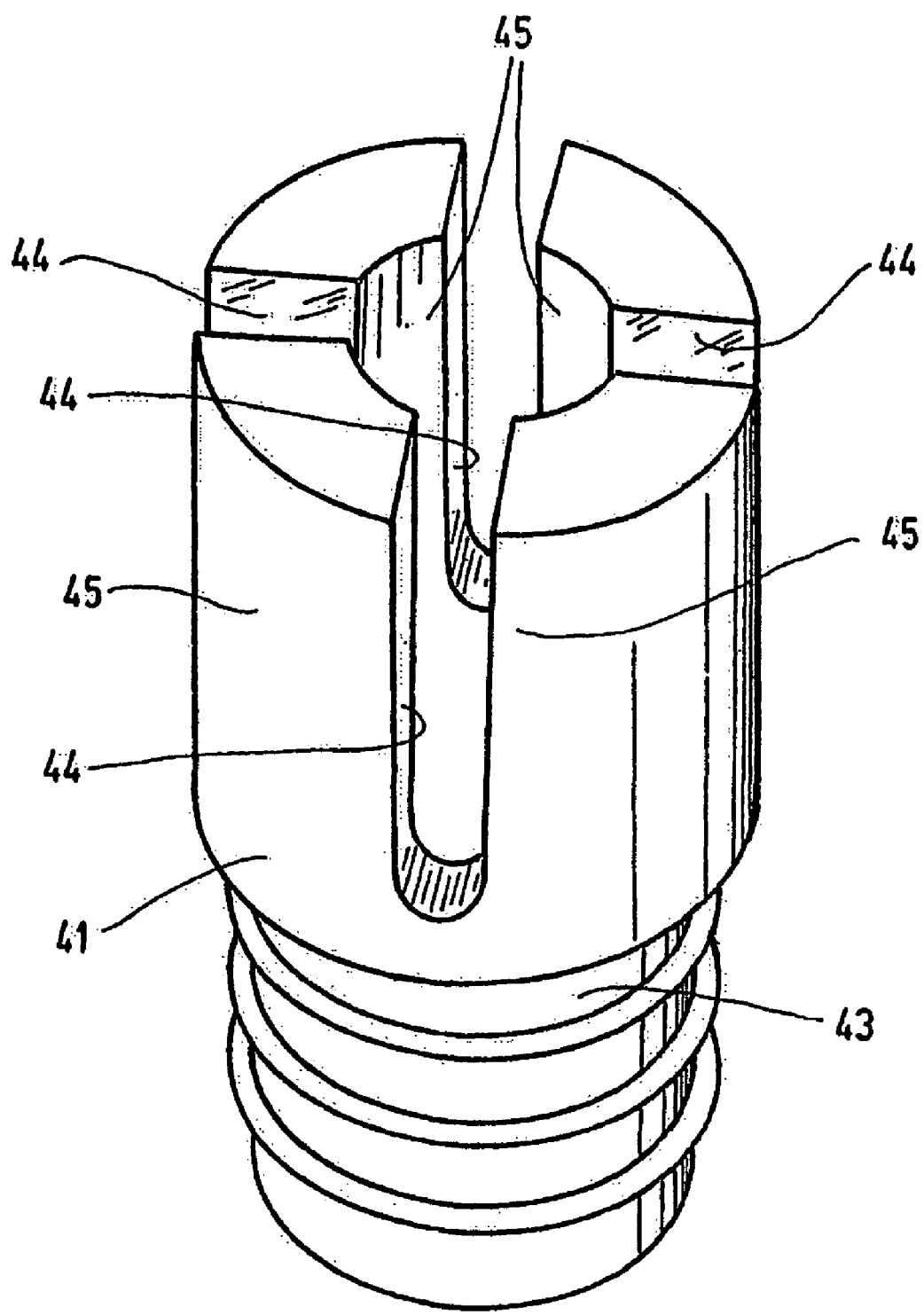
FIG. 14 is a highly enlarged perspective view of a blocking element designed as a collet for the distal end of the catheter tube of FIG. 1.

FIG. 14 shows the blocking element 41 separately. The blocking element 41 is a tube piece 43 which lengthens the catheter tube 1 and which has longitudinal slots 44 in its end part so that jaws 45 are formed as a kind of collet and under normal conditions reduce the passage clearance of the tube piece 43. The passage of the receiving part 33 in a slightly elastic way spreads the jaws 45 which assume the blocking position shown in FIGS. 5 to 13 after emergence of the receiving part 33, so that the receiving part 33, having emerged, is supported against moving backward. A central, projecting shoulder 47 of the receiving part 33 engages as a centering piece between the jaws 45 of the blocking element 41.

Figure 5:
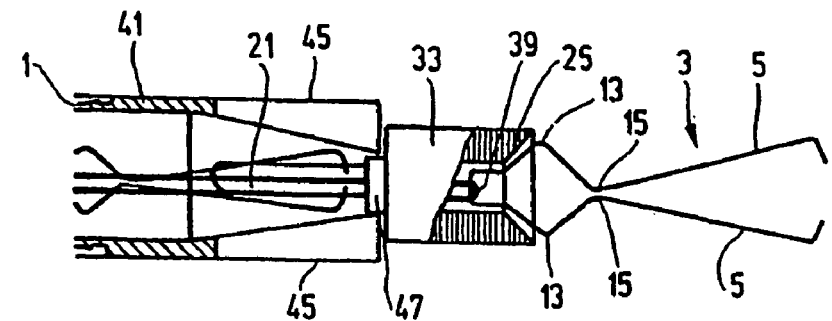
FIGS. 5 to 13 are schematic, side elevational views of only the distal (front) end of the catheter tube of FIG. 1, with the clip having emerged and with the respective sleeve-like receiving part, successive operating states being shown as the opening and closing cycle of the clip proceeds.
Figure 6:
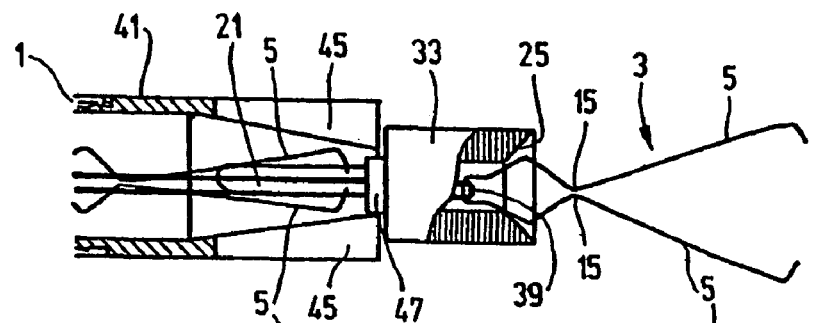
Figure 7:
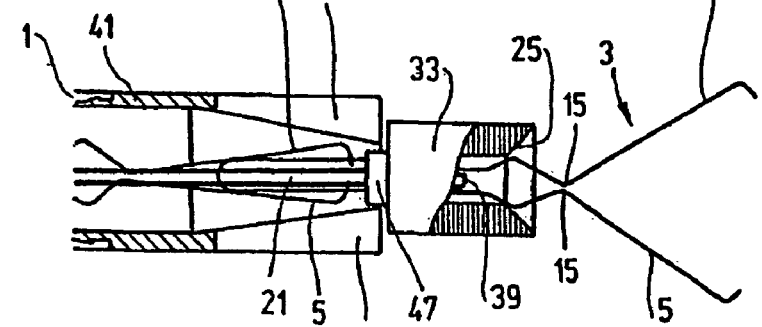
Figure 8:
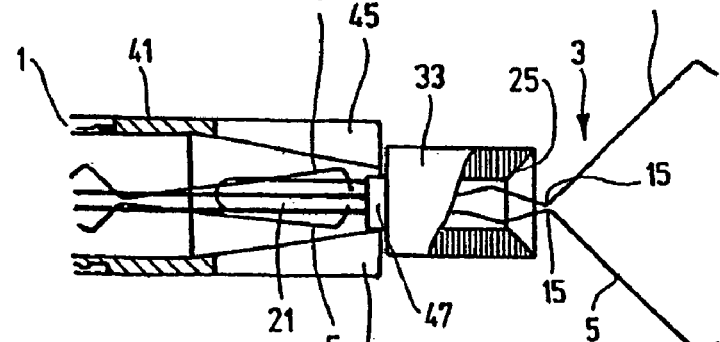

FIGS. 5 to 13 illustrate in a highly simplified schematic the progression of the opening and closing cycle of the clip 3 with the receiving part 33, which clip is to be applied and which has been pushed out of the blocking element 41. This entire cycle is effected by pulling on the pull cable 21. FIG. 5 shows the clip 3 activated for application with the sleeve-like receiving part 33 having been pushed out of the blocking element 41, the clip 3 not yet having been pulled into the receiving part 33 by the pull cable 21 to the extent that the first kinks 13 of the legs 5 would strike the beveled control surface 25 of the receiving part 33. The beveled control surface 25 corresponds to the oblique surface 25 on the sleeve 17 already discussed using the operating diagrams 3 and 4.

Figure 9:
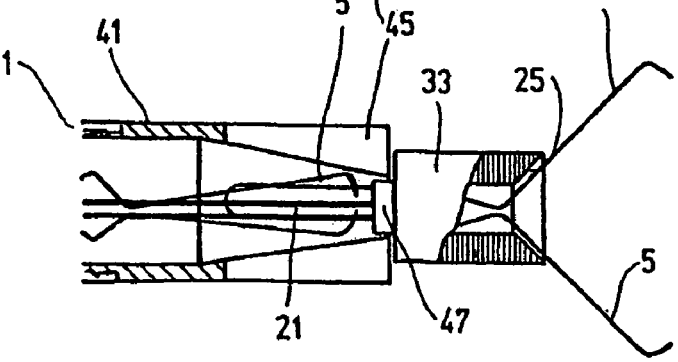
Figure 10:
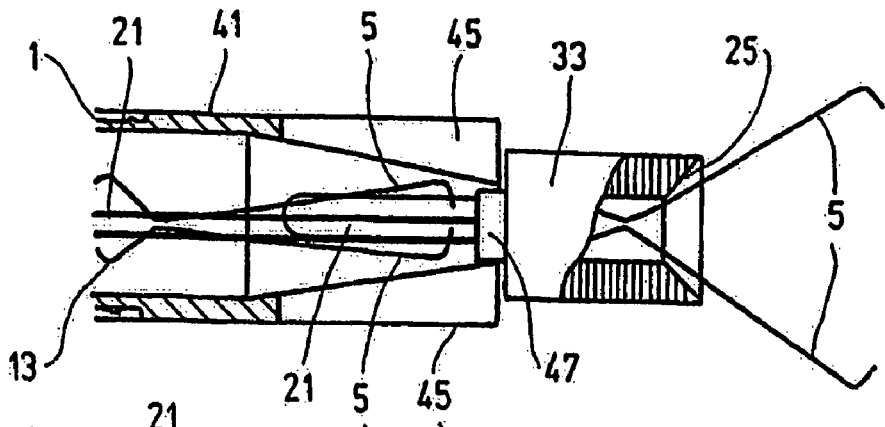
Figure 11:
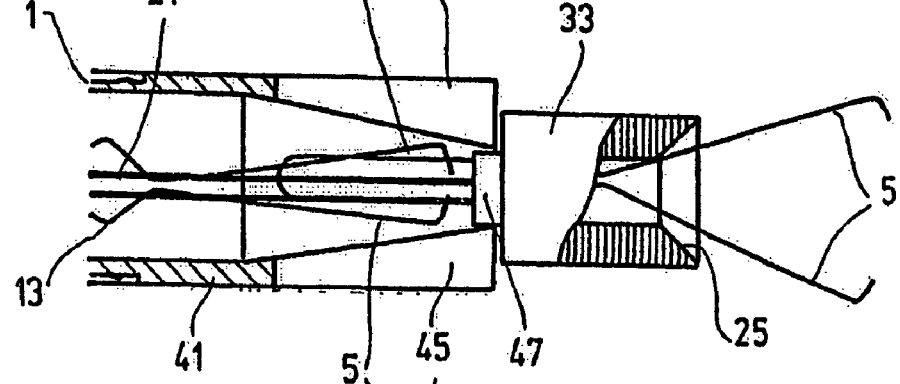
Figure 12:
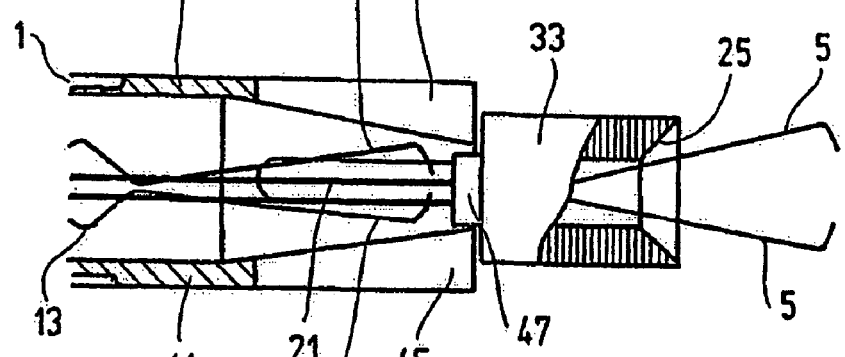
Figure 13:
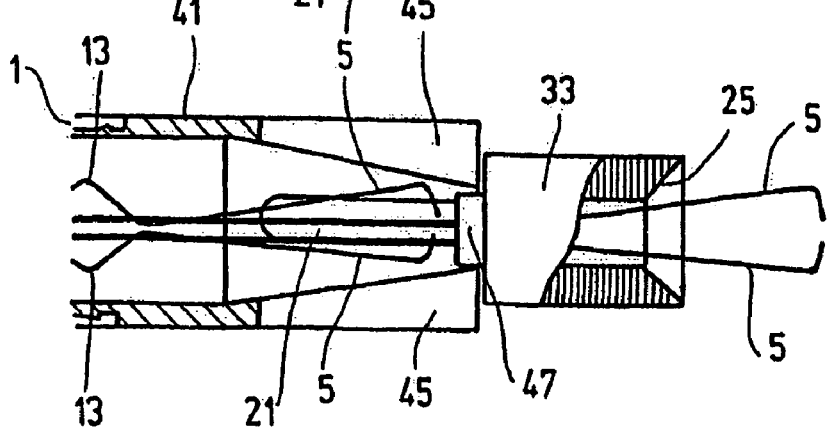

FIGS. 6 to 9 show the operating states which arise in succession by pulling the pull cable 21. The legs 5 of the clip are progressively opened by the first kinks 13 striking the control surface 25 until the state of complete opening is reached as shown in FIG. 9.

FIGS. 10 to 13 shows the closing cycle which results as the pull cable 21 continues to be pulled. The legs 5 close due to the inherent elasticity of the clip 3 and/or its deformation being completely released, as soon as the clip 3 has been pulled correspondingly far through the receiving part 33 such that an opening force is no longer being applied by the first kinks 13. This state is reached when the clip 3 is being pulled further beyond the position shown in FIG. 13 through the receiving part 33. After application which has taken place by the closing of the clip 3 at the hemorrhage site to be treated to completely release the applied clip 3, the pull cable 21 continues to be pulled to detach the pull cable from the applied clip. The applied clip is supported with its end having the end crosspiece 9 (FIG. 2) on the leg end 7 of the clip 3 following next in the catheter tube 1 or on the end edge 37 of the sliding tube 35. This detaching takes place by pulling harder on the pull cable 1 to apply a detachment force. Preferably, in one alternative embodiment, instead of the respective clip being supported on a following clip in the magazine when the pull cable 21 is pulled off, support is accomplished preferably exclusively by the sleeve-like receiving part 33. For this support, the clip at least partially transversely to its opening direction has blade-like widenings (not shown) on the legs 5 between the leg end 7 and the assignable second kink 15 and oppositely adjacent to the second kink, which widenings permit an interlocking option of the clip 3 in the sleeve-like receiving part 33 so that the necessary opposing holding force is thus formed for pulling off the pull cable 21 by the predetermined breaking point 51. This blade-like widening adjoins flanking on either side of the respective leg 5 of the clip 3.

Figure 2A:
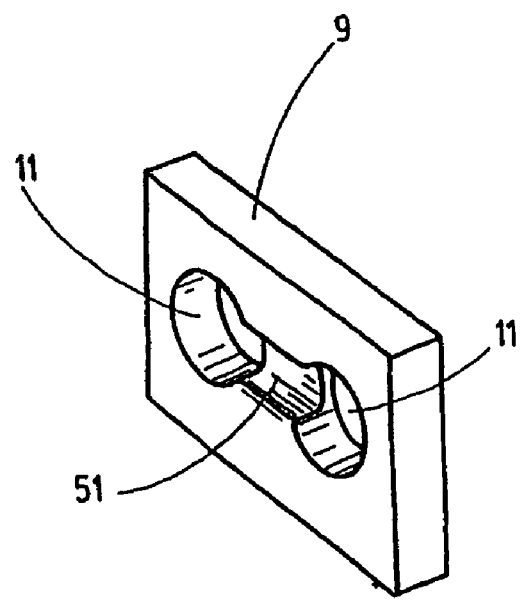
FIG. 2a is a further enlarged perspective view of only the end crosspiece of the clip of FIG. 2, which crosspiece is provided with a predetermined breaking point.

As can be clearly seen in FIG. 2a, for this purpose, in the end crosspiece 9 connecting the legs 5 of the clip 3 on the back end, between the through holes 11, a predetermined breaking point 51 is dimensioned such that the loop 39 of the pull cable 21 effects tearing through of the predetermined breaking point 51 when a predetermined pulling force is applied, which in practical embodiments is approximately 40 N. The applied clip 3 with the associated receiving part 33 thus remains at the treatment site, while after the process of tearing off, the pull cable 21 as a loop 39 automatically adjoins the end crosspiece 9 of the following clip which can be advanced by pushing forward by the sliding tube 35 for the immediately following application process.

The predetermined breaking point 51 can be made as shown in FIG. 2. It is also possible to make the predetermined breaking point from a different material which can be easily torn and which is different from that remaining material of the end crosspiece 9. Furthermore, it is also possible to make the end crosspiece 9 uniform in its material to form the predetermined breaking point and the end crosspiece 9 tears if a definable maximum force is exceeded with the pull cable 21.

The collet shown in FIG. 14 is fixed with its tube piece 43 as shown in FIG. 1 on the inside circumference of the free end of the catheter tube 1. It is also possible for the tube piece 43 to enclose the respective free end of the catheter tube 1 and to be held seated there by an adhesive connection and/or force fit.

As is to be seen, the entire application process can be carried out by pulling on the pull cable which is provided as the actuation element and which can be a fine steel cable. For the opening of the respectively activated clip 3 by pulling into the receiving part 33, the release of the pivoting motion of the legs 5 by pulling through the receiving part 33, and the detachment of the pull cable 21 by tearing the predetermined breaking point 51, the pull cable is moved automatically into contact with the end crosspiece 9 of the following clip 3 in the catheter tube 1. The device is then again immediately ready for the following application process. With the device of the present invention, it is possible to stop hemorrhages. The clip can also be used for marking purposes, for example, in the field of diagnostics. Also, surgical procedures can be carried out in which the clip is used as a surgical instrument, for example, for removing polyps in the gastrointestinal tract or the like.

While one embodiment has been chosen to illustrate the invention, it will be understood by those skilled in the art that various changes and modifications can be made therein without departing from the scope of the invention as defined in the appended claims.

What is claimed is:

1. A method for endoscopic application of self-closing medical clips, comprising the steps of:
   placing a distal end of a catheter tube in a body of a living being to be treated;
   arranging at least one self-closing medical clip with relatively movable legs in the catheter tube adjacent the distal end by an operator located on a proximal end of the catheter tube, the clip having a first kink in a first area of each leg extending outwardly and increasing a distance between the legs and a second kink in a second area nearer a distal leg end of the clip than the first area but spaced from the distal leg end extending inwardly and forming a point of mutual support for the legs;
   pushing the clip out of the distal end;
   opening the clip by an actuator having an actuating element with a pull cable acting on the clip, being movable longitudinally in the catheter tube, being actuated by the operator and having a control part converting an actuating force of the actuating element into a motion opening the legs of the clip, the clip being connected to the pull cable by a rear end crosspiece connecting the legs of the clip, the rear end crosspiece having two adjacent through holes through which the pull cable extends in a loop connecting an advancing strand extending from the operator to the rear end crosspiece to a retreating strand extending to the operator from the rear end crosspiece, the crosspiece having a section between the through holes forming a predetermined breaking point; and
   detaching the actuating element from the clip after opening of the clip to release and close the legs of the clip to apply the clip and detaching the pull cable from the clip by applying a pulling force on the pull cable to fracture the predetermined breaking point.

2. A method according to claim 1 wherein
   the legs of the clip are symmetrical, are mirror images of one another and do not cross one another.

3. A method according to claim 1 wherein
   a plurality of other clips, similar to the one clip, are arranged in succession in the catheter tube; and after application of the clip at the distal end of the catheter tube, the actuator is functionally linked to the clip next following in the catheter tube.

4. A method according to claim 1 wherein
distal ends of the legs are bent toward one another at a location spaced from said second kinks.

5. A device for endoscopic application of self-closing medical clips in a body of a living being, comprising:
a catheter tube having a distal end placeable in the body and a proximal end placeable outside the body;
an operator at said proximal end;
an actuator extending in said catheter tube from said operator in an area adjacent said distal end, having an actuating element with a pull cable movable longitudinally in said catheter tube and controlled by said operator, and having at least one control part with a distal end edge on a sleeve-shaped receiving part; and
at least one clip adjacent to and directly engaging said distal end edge and having a part received in said actuating element and two adjacent legs, said legs having first kinks extending outwardly and increasing a distance between said legs in first areas of said legs and second kinks extending inwardly and forming a mutual support for said legs in second areas of said legs nearer to a distal leg end of said clip than said first area, but spaced from said distal leg end without said legs crossing one another, said clip being connected to said pull cable by a rear end crosspiece connecting said legs of said clip, said rear end crosspiece having two adjacent through holes through which said pull cable extends in a loop connecting an advancing strand extending from said operator to said rear end crosspiece to a retreating strand extending to said operator from said rear end crosspiece, said rear end crosspiece having a section between said through holes forming a predetermined breaking point fracturable by a pulling force of said pull cable via said loop thereof to detach said pull cable from said clip;
whereby said legs are opened by said first kinks engaging said control part when said clip is inserted into said sleeve-shaped receiving part which converts an actuating force of said actuating element into an opening motion of said legs with said second areas engaging one another.

6. A device according to claim 5 wherein
said distal end edge comprises an internal beveled control surface.

7. A device according to claim 5 wherein
said through holes are parallel and laterally offset.

8. A device according to claim 5 wherein
a blocking element is located on said distal end of said catheter tube, said blocking element permitting passage of said sleeve-shaped receiving part only in an exit direction forward from said catheter tube and supporting said sleeve-shaped receiving part against motion rearwardly into said catheter tube effected by the pulling force of said pull cable.

9. A device according to claim 8 wherein
said blocking element comprises a tube piece mounted on said distal end of said catheter tube and having an end part forming a collet with jaws extending longitudinally, said jaws normally biased to reduce a width of a passage through said collet in a normal position thereof, being elastically spreadable radially outwardly from the normal position by said sleeve-shaped receiving part passing through said passage and being returnable to the normal position to form a support for said sleeve-shaped receiving part against the pulling force of the pull cable after said sleeve-shaped receiving part emerged from said collet.

10. A device according to claim 9 wherein
said distal edge comprises an internal beveled control surface; and
sleeve-shaped receiving part comprises a back end opposite said beveled control surface with an axially projecting shoulder receivable in said collet to center said sleeve-shaped receiving part relative to said blocking element.

11. A device according to claim 5 wherein
at least one other clip and at least one other control part, similar to said one clip and said one control part, respectively, are mounted in succession with said one clip and said one control part in said catheter tube; and
said advancing strand and said retreating strand extend through respective through holes in a rear end crosspiece joining legs of said other clip.

12. A device according to claim 5 wherein
said actuator comprises a tube movable in said actuator tube and having an end edge forming a plunger contacting a facing back end of said sleeve-shaped receiving part.

13. A device according to claim 5 wherein
distal ends of said legs are bent toward one another at a location spaced from said second kinks.

14. A self-closing medical clip, comprising:
a crosspiece having two adjacent through holes therein and a predetermined breaking point extending between said through holes;
first and second legs extending adjacent one another from said crosspiece to distal ends thereof and biased toward one another, said crosspiece extending between and directly connecting adjacent ends of said legs;
a pull cable extending through said through holes in a loop connecting an advancing strand extending to said crosspiece and a retreating strand extending away from said crosspiece and laterally adjacent said advancing strand, said predetermined breaking point being fracturable by a pulling force of said pull cable via said loop to detach said cable from said crosspiece;
first kinks in said legs extending outwardly and increasing a distance between said legs in first areas of said legs; and
second kinks in said legs extending inwardly and forming a mutual support for said legs in second areas of said legs, said second areas being nearer said distal ends than said first areas but being spaced from said distal ends.

15. A self-closing medical clip according to claim 14 wherein
said legs do not cross one another.

16. A self-closing medical clip according to claim 14 wherein
said through holes are parallel and laterally offset.

17. A self-closing medical clip according to claim 14 wherein
said distal ends of said legs are bent toward one another at a location spaced from said second kinks.

18. A method for endoscopic application of self-closing medical clips, comprising the steps of:
placing a distal end of a catheter tube in a body of a living being to be treated;
arranging at least one self-closing medical clip with relatively movable legs in the catheter tube adjacent the distal end by an operator located on a proximal end of the catheter tube, the clip having a first kink in a first area of each leg extending outwardly and increasing a distance between the legs and a second kink in a second area nearer a distal leg end of the clip than the first area but spaced from the distal leg end extending inwardly and forming a point of mutual support for the legs;

pushing the clip out of the distal end;

opening the clip by an actuator having an actuating element with a pull cable acting on the clip, being movable longitudinally in the catheter tube, being actuated by the operator and having a control part converting an actuating force of the actuating element into a motion opening the legs of the clip by pressing on each first kink inwardly to cause the legs to pivot at and about the mutual support such that leg portions between the second kinks and distal leg ends open, the clip being connected to the pull cable by a rear end crosspiece connecting the legs of the clip, the rear end crosspiece having two adjacent through holes through which the pull cable extends in a loop connecting an advancing strand extending from the operator to the rear end crosspiece to a retreating strand extending to the operator from the rear end crosspiece, the crosspiece having a section between the through holes forming a predetermined breaking point; and detaching the actuating element from the clip after opening of the clip to release and close the legs of the clip to apply the clip by the resiliency of the clip alone without attaching another member to the clip and detaching the pull cable from the clip by applying a pulling force on the pull cable to fracture the predetermined breaking point.

* * * * *